US008480729B2

(12) United States Patent
Atanasoska et al.

(10) Patent No.: US 8,480,729 B2
(45) Date of Patent: Jul. 9, 2013

(54) MEDICAL DEVICES CONTAINING SILICATE AND CARBON PARTICLES

(75) Inventors: Liliana Atanasoska, Edina, MN (US); Jan Weber, Maastrichet (NL); John Jianhua Chen, Plymouth, MN (US); Daniel J. Horn, Shoreview, MN (US)

(73) Assignee: Boston Science Scimed, Inc., Maple Grove, MN (US)

( * ) Notice: Subject to any disclaimer, the term of this patent is extended or adjusted under 35 U.S.C. 154(b) by 954 days.

(21) Appl. No.: 12/205,647

(22) Filed: Sep. 5, 2008

(65) Prior Publication Data
US 2009/0149948 A1    Jun. 11, 2009

Related U.S. Application Data

(60) Provisional application No. 60/970,485, filed on Sep. 6, 2007.

(51) Int. Cl.
*A61L 29/02* (2006.01)
*A61L 29/16* (2006.01)
*A61L 31/02* (2006.01)
*A61L 31/16* (2006.01)

(52) U.S. Cl.
USPC ........ 623/1.42; 623/1.1; 604/523; 604/96.01; 977/742

(58) Field of Classification Search
None
See application file for complete search history.

(56) References Cited

U.S. PATENT DOCUMENTS

| | | | |
|---|---|---|---|
| 4,963,313 A | 10/1990 | Noddin et al. | |
| 5,195,969 A | 3/1993 | Wang et al. | |
| 5,270,086 A | 12/1993 | Hamlin | |
| 5,543,378 A | 8/1996 | Wang | |
| 5,556,383 A | 9/1996 | Wang et al. | |
| 5,591,312 A | 1/1997 | Smalley | |
| 5,733,925 A | 3/1998 | Kunz et al. | |
| 5,853,886 A | 12/1998 | Pinnavaia et al. | |
| 6,149,775 A | 11/2000 | Tsuboi et al. | |
| 6,312,303 B1 | 11/2001 | Yaniv et al. | |
| 6,545,097 B2 | 4/2003 | Pinchuk et al. | |
| 6,592,568 B2 | 7/2003 | Campbell | |
| 6,607,551 B1 | 8/2003 | Sullivan et al. | |
| 6,837,928 B1 | 1/2005 | Zhang et al. | |
| 6,866,801 B1 | 3/2005 | Mau et al. | |
| 7,727,541 B2 * | 6/2010 | Richard et al. ................ 424/423 |
| 2002/0068170 A1 | 6/2002 | Smalley et al. | |
| 2003/0068432 A1 | 4/2003 | Dai et al. | |
| 2003/0093107 A1 | 5/2003 | Parsonage et al. | |
| 2003/0133865 A1 | 7/2003 | Smalley et al. | |
| 2003/0143350 A1 * | 7/2003 | Jimenez ...................... 428/35.2 |
| 2003/0171257 A1 | 9/2003 | Stirbl et al. | |
| 2003/0180472 A1 | 9/2003 | Zhou et al. | |
| 2003/0185985 A1 | 10/2003 | Bronikowski et al. | |
| 2003/0236514 A1 | 12/2003 | Schwarz | |
| 2004/0038007 A1 | 2/2004 | Kotov et al. | |
| 2004/0073251 A1 | 4/2004 | Weber | |
| 2004/0136896 A1 | 7/2004 | Liu et al. | |
| 2004/0266063 A1 | 12/2004 | Montgomery et al. | |
| 2005/0038498 A1 | 2/2005 | Dubrow et al. | |
| 2005/0124976 A1 * | 6/2005 | Devens et al. ................ 604/523 |
| 2005/0140261 A1 | 6/2005 | Gilad | |
| 2005/0152891 A1 * | 7/2005 | Toone et al. .................. 424/125 |
| 2005/0181015 A1 | 8/2005 | Zhong | |
| 2005/0208100 A1 | 9/2005 | Weber et al. | |
| 2005/0260355 A1 | 11/2005 | Weber et al. | |
| 2006/0051535 A1 | 3/2006 | Arney et al. | |
| 2007/0154513 A1 | 7/2007 | Atanasoska et al. | |
| 2007/0207182 A1 | 9/2007 | Weber | |
| 2009/0104386 A1 * | 4/2009 | Barrera et al. ................ 428/34.1 |
| 2011/0045179 A1 * | 2/2011 | Resasco et al. ............... 427/202 |

FOREIGN PATENT DOCUMENTS

| | | |
|---|---|---|
| DE | 4023787 A1 | 12/1991 |
| WO | 0130694 | 5/2001 |
| WO | 03026532 A2 | 4/2003 |
| WO | 03103854 | 12/2003 |
| WO | 2004053112 | 6/2004 |
| WO | 2004096085 | 11/2004 |
| WO | 2005079754 | 9/2005 |

OTHER PUBLICATIONS

S. Peeterbroeck, et al., "Polymer-layered silicate-carbon nanotube nanocomposites: unique nanofiller synergistic effect," Composites Science and Technology, vol. 64: 2317-2323, 2004.
Yinzhong Guo, et al., "Multi-layer LB films of single-wall carbon nanotubes," Physica B. vol. 323 (2002): 235-236.
Yinzhong Guo, et al., "Manipulation of single-wall carbon nanotubes into aligned molecular layers," Chemical Physics Letters, vol. 362 (2002): 314-314.
Z.S. Rak, "Advanced Forming Techniques in Ceramics," May 2000, ECN-RX-00-003, 18 pp.
Ralph Krupke, et al., "Separation of Metallic from Semiconducting Single-Walled Carbon Nanotubes," Science, vol. 301, Jul. 18, 2003, 344-347.
Torsten Prasse, et al., "Electric anisotrophy of carbon nanofibre/epoxy resin composites due to electric field induced alignment," Composites Science and Technology, vol. 63 (2003):1835-1841.

(Continued)

*Primary Examiner* — Suzanne Ziska
(74) *Attorney, Agent, or Firm* — Seager, Tufte & Wickhem, LLC

(57) ABSTRACT

According to one aspect of the present invention, implantable and insertable medical devices are provided which contain one or more particle-containing regions that comprise silicate particles and carbon particles.

25 Claims, 1 Drawing Sheet

OTHER PUBLICATIONS

C.A. Martin, et al., "Electric field-induced aligned multi-wall carbon nanotube networks in epoxy composites," Polymer, vol. 46 (2005): 877-886.
Jakub Wojturski et al., "Electrical Conductivity of Polyaniline Suspensions 2. Freezing-Melting Cycle," Croactica Chemica Acta, vol. 71 No. 4 (1998): 873-882.
Kannan Balasubramanian, et al., "Chemically Functionalized Carbon Nanotubes," Small vol. 1, No. 2 (2005):180-192.
T. Ramanathan et al., "Amino-Functionalized Carbon Nanotubes for Binding to Polymers and Biological Systems," Chem. Mater, vol. 17 (2005): 1290-1295.
Chungui Zhao et al., "Functionalized carbon nanotubes containing isocyanate groups," Journal of Solid State Chemistry, vol. 177 (2004): 4394-4398.
Sarbajit Banerjee et al., "Covalent Surface Chemistry of Single-Walled Carbon Nanotubes," Advanced Materials, vol. 17, No. 1 (2005): 17-29.
Durairaj Baskaran et al. "Polymer adsorption in the grafting reactions of hydroxyl terminal polymers with multi-walled carbon nanotubes," Polymer, vol. 46 (2005):5050-5057.
Enzo Menna et al., "Shortened single-walled nanotubes functionalized with poly(ethylene glycol): preparation and properties." Arkivoc, (xiii):64-73, 2003.
Richard Czerw et al., "Organization of Polymers onto Carbon Nanotubes: A Route to Nanoscale Assembly," Nano Letters, vol. 1, No. 8 (2001):423-427.
Yuanqin Liu et al., "Functionalization of Single-Walled Carbon Nanotubes with Well-Defined Polymers by Radical Coupling," Macromolecules, vol. 38 (2005):1172-1179.
Jeffrey Pyun et al., "Synthesis of Nanocomposite Organic/Inorganic Hybrid Materials Using Controlled/"Living" Radical Polymerization," Chem. Mater., vol. 13 (2001): 3436-3448.
Hao Kong et al., "Controlled Functionalization of Single-Walled Carbon Nanotubes by in Situ Atom Transfer Radical Polymerization," J. Am. Chem. Soc., vol. 126 (2004): 412-413.
Zhaoling Yao et al., "Polymerization from the surface of Single-Walled Carbon Nanotubes—Preparation and Characterization of Nanocomposites," J. Am. Chem. Soc., vol. 125 (2003):16015-16024.
Shuhui Qin et al., "Functionalization of Single-Walled Carbon Nanotubes with Polystyrene via Grafting to and Grafting from Methods," Macromolecules, vol. 37 (2004): 752-757.
Yuanqin Liu et al., "Preparation and Utilization of Catalyst-Functionalized Singe-Walled Carbon Nanotubes for Ring-Opening Metathesis Polymerization," Macromolecules, vol. 37 (2004): 4755-4760.
Gunaranjan Viswanathan et al., "Single-Step in Situ Synthesis of Polymer-Grafted Single-Wall Nanotube Composites," J. Am. Chem. Soc., vol. 125 (2003): 9258-9259.
Changchun Wang et al., "Polymers containing fullerene or carbon nanotube structures," Progress in Polymer Science, vol. 29 (2004): 1079-1141.
Zhonghua Peng, "Rational Synthesis of Covalently Bonded Organic-Inorganic Hybrids," Agnew Chem. Int. Ed, vol. 43 (2004):930-936.
Aaron R. Moore et al., "Organoimido-polyoxometalates as polymer pendants," Chem. Commun., 2000: 1793-1794.
Hu Changwen et al., "Polyoxometalate-based organic-inorganic hybrid materials," C.L.I., 3(6), Jun. 1, 2001.
Pingfan Wu et al., "An Easy Route to Monofunctionalized Organoimido Derivatives of the Lindqvist Hexamolybdate," Eur.J. Inorg. Chem., 2819-2822, 2004.
Meng Lu et al., "Synthesis of Main-Chain Polyoxometalate-Containing Hybrid Polymers and Their Applications in Photovoltaic Cells," Chem. Mater., vol. 17, No. 2: 402-408, 2005.
Jishuang Zhang et al., "Improving multilayer films endurance by photoinduced interaction between Dawson-type polyoxometalate and diazo resin," Materials Chemistry and Physics, vol. 90 (2005): 47-52.
Chao Qin et al., "A linear bifunctionalized organoimido derivative of hexamolybdate: Convenient synthesis and crystal structure," Inorganic Chemistry Communications, vol. 8 (2005): 751-754.
Jun Yang et al., "Preparation and characterization of positively charged ruthenium nanoparticles," Colloid and Interface Science, vol. 271 (2004): 308-312.
R.A. Roesner et al., "Mono-and di-functional aromatic amines with p-alkoxy substituents as novel arylimido ligands for the hexamolybdate ion," Inorganica Chimica. Acta, vol. 342 (2003): 37-47.
R. Viitala et al., "Surface properties of in vitro bioactive and non-bioactive sol-gel derived materials," Biomaterials, vol. 23 (2002): 3073-3086.
C.A. Martin et al., "Formation of percolating networks in multiwall carbon-nanotube-epoxy composites," Composites Science and Technology, vol. 64 (2004): 2309-2316.
Jong Kuk Lim et al., "Selective thiolation of single-walled carbon nanotubes." Synthetic Materials, vol. 139 (2003): 521-527.
Valerie C. Moore et al., "Individually Suspended Single-Walled Carbon Nanotubes in Various Surfactants," Nano Letters, vol. 3 (2003): 1379-1382.
Dimitrios Tasis et al., "Soluble Carbon Nanotubes," Chem. Eur. J., vol. 9 (2003): 4000-4008.
Yu-Hsuan Liao et al., "Investigation of the dispersion process of SWNTs/SC-15 epoxy resin nanocomposites," Materials Science & Engineering A, vol. 385: 175-181, 2004.
Dae-Hwan Jung et al., "Aggregation behavior of chemically attached poly(ethylene glycol) to single-walled carbon nanotubes (SWNTs) ropes," Materials Science and Engineering C, vol. 24: 117-121, 2004.
"Electric-field aligned CNT composites," Materials Today, pp. 12, Feb. 2005.
Dong Cai et al., "Highly efficient molecular delivery into mammalian cells using carbon nanotube spearing," Nature Methods, vol. 2, No. 6: 449-454, Jun. 2005.
Zhenhui Kang et al., "Polyoxometalates nanoparticles: synthesis, characterization and carbon nanotube modification," Solid State Communications, vol. 129: 559-564, 2004.
Ulrich Schubert, "Polymers Reinforced by Covalently Bonded Inorganic Clusters," Chem. Mater., vol. 13, No. 10: 3487-3494, 2001.
L. Xu et al., "Stable multilayer films based on photoinduced interaction between polyoxometalates and diazo resin," Materials Letters, vol. 58: 3441-3446, 2004.
Brenda L. Hurley et al., "Covalent Bonding of Organic Molecules to Cu and AL Alloy 2024 T3 Surfaces via Diazonium Ion Reduction," Journal of the Electrochemical Society, vol. 151: B252-B259, 2004.
Michael R. Diel et al., "Self-Assembled, Deterministic Carbon Nanotube Wiring Networks," Agnew Chem. Int. Ed., vol. 41, No. 2: 353-356, 2002.
P.J. Burke, "Nanodielectrophoresis: Electronic Nanotweezers," Encyclopedia of Nanoscience and Nanotechnology, ed. H.S. Nalwa, vol. 10, pp. 1-19 (American Scientific Publishers, 2003).
Paul Jaynes, et al, "Alignment and Deposition of Single Wall Carbon Nanotubes Under the Influence of an Electric Field," Materials Research Society Symposium Proceedings, vol. 761E, pp. 115-120, 2003.
Jenny M. Hilding, et al., "Alignment of Dispersed Multiwalled Carbon Nanotubes in Low Strength AC Electrical Fields," Journal of Nanoscience and Nanotechnology, vol. 5, pp. 742-746, 2005.
Donglu Shi, et al., "Magnetic Alignment of Carbon Nanofibers in Polymer Composites and Anisotrophy of Mechanical Properties," Journal of Applied Physics, American Institute of Physics, vol. 97, No. 6, pp. 64312 (3 pages), Mar. 11, 2005.
Christian P. Deck, "Prediction of carbon nanotube growth success by the analysis of carbon-catalyst binary phase diagrams," Carbon, 44: 267-275, 2006.
Kin-tak Lau et al., "Cobalt hydroxide colloidal particles precipitation on nanoclay layers for the formation of novel nanocomposites of carbon nanotubes/nanoclay," Composites Science Technology, 66: 450-458, 2006.
Mei Lu et al., "Enhancement of Vicker's hardness of nanoclay-supported nanotube reinforced novel polymer composites," Carbon, 44(2): 383-386, 2006.
Yuri Lvov et al., "Molecular film assembly via layer-by-layer adsorption of oppositely charged macromolecules (linear polymer, protein and clay) and concanavalin A and glycogen," Thin Solid Films, 284-285 (1996), 797-801.

* cited by examiner

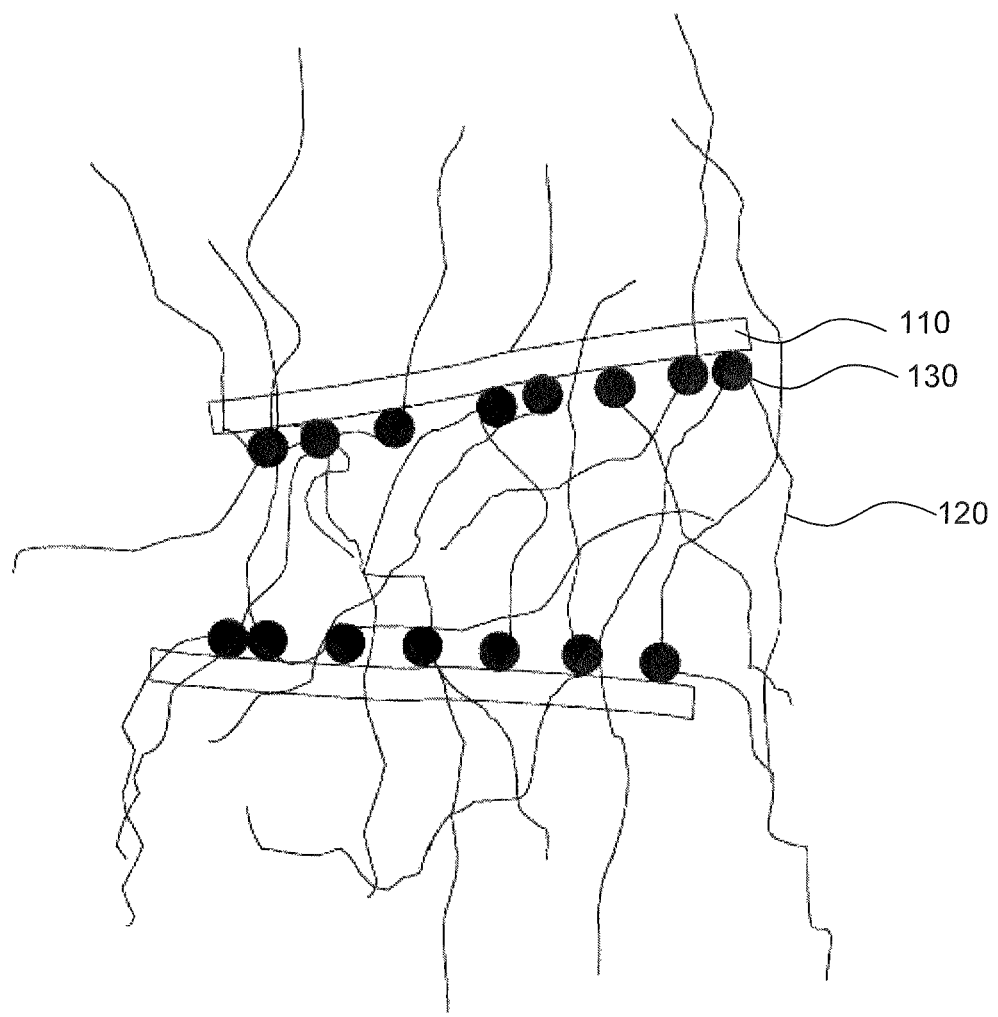

MEDICAL DEVICES CONTAINING SILICATE AND CARBON PARTICLES

RELATED APPLICATION

This application claims the benefit of U.S. Provisional Application Ser. No. 60/970,485, filed on Sep. 6, 2007, the entire disclosure of which is incorporated herein by reference. This application is also related to WO 2005/115496, U.S. Patent Application Pub. No. US 2005/0181014, U.S. Patent Application Pub. No. US 2005/0181015, and U.S. Patent Application Pub. No. US 2007/0207182, the entire disclosures of which are all herein incorporated by reference.

FIELD OF THE INVENTION

The present invention relates to medical devices that comprise silicate particles and carbon particles.

BACKGROUND OF THE INVENTION

The inclusion of particles is known to provide various materials with modified properties. For example, layered silicates, such as those found in clays, have been employed to reduce the permeability of polymer compositions, which may be used, for instance, as barrier coatings for inflatable articles such as sports balls. See, e.g., U.S. Pat. No. 6,232,389 to Feeney et al. Such particles have also been described in conjunction with the delivery of therapeutic agents from polymer-containing regions of medical articles. See U.S. Pub. No. 2005/0181014 to Richard and U.S. Pub. No. 2005/0181015 to Zhong. As another example, carbon nanotubes have been reported for use in creating thin, flexible, high strength multilayer components for medical devices such as balloons, among others. See WO 2005/115496 to Chen et al.

SUMMARY OF THE INVENTION

According to an aspect of the invention, medical devices are provided which contain one or more particle-containing regions that comprise silicate particles and carbon particles. The medical devices are configured for implantation or insertion into a subject.

The above and other aspects, as well as various embodiments and advantages of the present invention will become immediately apparent to those of ordinary skill in the art upon reading the disclosure to follow.

BRIEF DESCRIPTION OF THE DRAWING

FIG. 1 is a schematic illustration of silicate-supported carbon nanotubes in accordance with the prior art.

DETAILED DESCRIPTION OF THE INVENTION

According to one aspect of the present invention, implantable and insertable medical devices are provided which contain one or more particle-containing regions that comprise silicate particles and carbon particles (referred to herein collectively as "silicate/carbon particles", whether attached or unattached to one another).

The particle-containing regions typically further comprise one or more supplemental materials other than silicate particles and carbon particles, for example, a supplemental polymeric and/or a ceramic material, among other possibilities.

In some embodiments, the medical devices of the invention further comprise one or more optional therapeutic agents, in other embodiments they do not. "Therapeutic agents," "drugs," "biologically active agents," "pharmaceutically active agents," and other related terms may be used interchangeably herein.

Examples of medical devices benefiting from the present invention vary widely and include implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglielmi detachable coils and metal coils), septal defect closure devices, drug depots that are adapted for placement in an artery for treatment of the portion of the artery distal to the device, myocardial plugs, patches, pacemakers, leads including pacemaker leads, defibrillation leads and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, tacks for ligament attachment and meniscal repair, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, or other devices that are implanted or inserted into the body.

The medical devices of the present invention include, for example, implantable and insertable medical devices that are used for systemic treatment or diagnosis, as well as those that are used for the localized treatment or diagnosis of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, brain, lungs, trachea, esophagus, intestines, stomach, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Subjects are vertebrate subjects, more typically mammalian subjects including human subjects, pets and livestock.

In some embodiments, the particle-containing regions for use in the medical devices of the invention correspond to entire medical devices. In other embodiments, the particle-containing regions correspond to one or more portions of a medical device. For instance, the particle-containing regions can be in the form of medical device components, in the form of one or more fibers which are incorporated into a medical device, in the form of one or more layers formed over all or only a portion of an underlying substrate corresponding to a medical device or a component thereof, and so forth. Layers can be provided over an underlying substrate at a variety of locations, and in a variety of shapes or patterns (e.g., in the form of a series of rectangles, stripes, or any other continuous or non-continuous pattern). As used herein a "layer" of a given material is a region of that material whose thickness is small compared to its length and width (e.g., 10% or less). As used herein a layer need not be planar, for example, taking on the contours of an underlying substrate. Layers can be discontinuous (e.g., patterned). Terms such as "film," "layer" and "coating" may be used interchangeably herein.

Substrate materials for particle-containing regions in accordance with the present invention may vary widely in composition and are not limited to any particular material. They can be selected from a range of biostable materials (i.e., materials that, upon placement in the body, remain substantially intact over the anticipated placement period for the device) and biodisintegrable materials (i.e., materials that, upon placement in the body, are dissolved, degraded, resorbed, and/or otherwise removed from the placement site over the anticipated placement period), including (a) organic materials (i.e., materials containing organic species, typically 50 wt % or more, for example, from 50 wt % to 75 wt % to 90 wt % to 95 wt % to 97.5 wt % to 99 wt % or more) such as polymeric materials and biologies, (b) inorganic materials (i.e., materials containing inorganic species, typically 50 wt % or more, for example, from 50 wt % to 75 wt % to 90 wt % to 95 wt % to 97.5 wt % to 99 wt % or more), such as metallic materials (i.e., materials containing metals, typically 50 wt % or more, for example, from 50 wt % to 75 wt % to 90 wt % to 95 wt % to 97.5 wt % to 99 wt % or more) and non-metallic inorganic materials (i.e., materials containing non-metallic inorganic materials, typically 50 wt % or more, for example, from 50 wt % to 75 wt % to 90 wt % to 95 wt % to 97.5 wt % to 99 wt % or more) (e.g., carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others), and (c) hybrid materials (e.g., hybrid organic-inorganic materials, for instance, polymer/metallic inorganic and polymer/non-metallic inorganic hybrids).

Specific examples of inorganic non-metallic materials may be selected, for example, from materials containing one or more of the following: metal oxide ceramics, including aluminum oxides and transition metal oxides (e.g., oxides of titanium, zirconium, hafnium, tantalum, molybdenum, tungsten, rhenium, iron, niobium, iridium, etc.); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based ceramic-like materials such as carbon nitrides.

Specific examples of metallic materials may be selected, for example, from metals such as gold, iron, niobium, platinum, palladium, iridium, osmium, rhodium, titanium, tantalum, tungsten, ruthenium, and magnesium, among others, and alloys such as those comprising iron and chromium (e.g., stainless steels, including platinum-enriched radiopaque stainless steel), niobium alloys, titanium alloys, alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodisintegrable alloys including alloys of magnesium, zinc and/or iron (including their alloys with combinations of each other and Ce, Ca, Zr, Li, etc.), among others.

Specific examples of organic materials include polymers, which may be selected from those described below for use as supplemental materials in the particle-containing regions.

As noted above, in one aspect, the invention provides implantable and insertable medical devices which contain one or more particle-containing regions that comprise silicate particles and carbon particles (which, as also noted above, are referred to herein collectively as "silicate/carbon particles," whether attached or unattached to one another).

The amount of silicate/carbon particles within the particle-containing regions can vary widely and may represent, for example, from 1 wt % or less to 2 wt % to 5 wt % to 10 wt % to 25 wt % to 50 wt % to 75 wt % to 90 wt % to 95 wt % to 98 wt % to 99 wt % or more of the particle-containing region.

Carbon particles in accordance with the invention include carbon nanofibers and carbon nanotubes, which typically have widths of 1000 nm or less. Carbon nanotubes are particles that are understood to comprise molecular carbon that is predominantly in $sp^2$ hybridized form (i.e., structures in which the carbons atoms are predominantly connected to three other carbon atoms within a lattice structure, sometimes referred to as a "grapheme carbon lattice"). For example, while graphite molecules contain planar sheets of $sp^2$ hybridized carbon, carbon nanotubes have been described as curved sheets of $sp^2$ hybridized carbon in the form of hollow tubes. Carbon nanotubes may thus be thought of as one or more sheets of graphite that are shaped into tubes and, in fact, have been made by directing a laser at a graphite surface, causing some of the sheets to be displaced from the graphite, which subsequently react to form nanotubes. Specific examples of nanotubes include single-wall carbon nanotubes (SWCNTs) and multi-wall carbon nanotubes (MWCNTs) (i.e., nanotubes having walls that are two or more carbon layers thick). SWCNTs have typical inner diameters ranging from 0.25 nm to 0.5 nm to 1 nm to 2.5 nm to 5 nm, and typical lengths up to 100 micron (jam) or more, for example, lengths ranging from 10 nm to 100 nm to 1 micron to 10 microns to 100 microns or more. MWCNTs have typical inner diameters ranging from 2.5 nm to 5 nm to 10 nm, outer diameters of 5 nm to 10 nm to 25 nm to 50 nm, and typically lengths up to 100 microns or more, for example, lengths ranging from 10 nm to 100 nm to 1 micron to 10 microns to 100 microns or more.

As used herein "silicates" are particles that contain covalently bound silicon and oxygen having a net negative charge which is offset by the presence of one or more types of counterions. In many silicates, including silicate minerals, a silicon atom is in tetrahedral coordination with four oxygen atoms. In different minerals, the tetrahedra exhibit different degrees of repetition, for example, occurring singly (e.g., olivine), in pairs (e.g., epidote), and in larger finite clusters including rings (e.g., the tourmaline group), chains (e.g., the pyroxene group), double chains (e.g., the amphibole group) and sheet-like particles (e.g., phyllosilicates such as micas and clays). In many embodiments, the silicate particles employed in the practice of the invention are phyllosilicates, which may be either exfoliated or non-exfoliated (e.g., in the form of stacked silicate sheets). As used herein a "silicate sheet" is a silicate whose thickness is small compared to its length and width (e.g., 10% or less).

The spacing between the adjacent layers within non-exfoliated phyllosilicate particles is typically in the range of 5-20 A. Phyllosilicate particles for the practice of the present invention can be selected from natural and synthetic versions of following: (a) allophane; (b) apophyllite; (c) bannisterite; (d) carletonite; (e) cavansite; (f) chrysocolla; (g) members of the clay group, including: (i) members of the chlorite group such as baileychlore, chamosite, chlorite, clinochlore, cookeite, nimite, pennantite, penninite, sudoite, (ii) glauconite, (iii) Mite, (iv) kaolinite, (v) montmorillonite, (vi) palygorskite, (vii) pyrophyllite, (viii) sauconite, (ix) talc, and (x) vermiculite; (h) delhayelite; (i) elpidite; (j) fedorite; (k) franklinfurnaceite; (l) franklinphilite; (m) gonyerite; (n) gyrolite; (o) leucosphenite; (p) members of the mica group, including (i) biotite, (ii) lepidolite, (iii) muscovite, (iv) paragonite, (v) phlogopite, and (vi) zinnwaldite; (q) minehillite; (r) nordite; (s) pentagonite; (t) petalite; (u) prehnite; (v) members of the serpentine group, including (i) antigorite, (ii) clinochrysotile, (iii) lizardite, (iv) orthochrysotile and (v) serpentine; (w) rhodesite; (x) sanbomite; (y) wickenburgite; (z) zeophyllite; and mixtures thereof.

Additional phyllosilicate particles for the practice of the present invention, not necessarily exclusive of those above, can be selected from natural and synthetic versions of following: aliettite, swinefordite, yakhontovite, volkonskoite, stevensite, hectorite, magadiite, kenyaite, ledikite, laponite, saponite, sauconite, montmorillonite, bentonite, nontronite, beidellite, hectorite, other smectite group clays, and mixtures thereof.

Further phyllosilicate particles for the practice of the present invention, not necessarily exclusive of those above, can be selected from natural and synthetic versions of following: (a) planar hydrous phyllosilicates such as those of the serpentine-kaolin group, talc-pyrophyllite group, smectite group, vermiculite group, true (flexible) mica group, brittle mica group or chorite group, for example, lizardite, berthierine, amesite, cronstedtite, nepouite, kellyite, fraipontite, brindleyite, kaolinite, dickite, nacrite, halloysite (planar), odinite, talc, willemseite, kerolite, pimelite, pyrophyllite, ferripyrophyllite, saponite, hectorite, sauconite, stevensite, swinefordite, montmorillonite, beidellite, nontronite, volkonskoite, trioctahedral vermiculite, dioctahedral vermiculite, biotite, phlogopite, lepidolite, muscovite, illite, glauconite, celadonite, paragonite, clintonite, kinoshitalite, bityite, anandite, margarite, clinochlore, chamosite, pennantite, nimite, baileychlore, donbassite, cookeite, sudoite, corrensite, aliettite, hydrobiotite, kulkeite, rectorite or tosudite and (b) non-planar hydrous phyllosilicates, for example, antigorite, bemenitite, greenalite, caryopilite, pyrosmalite, manganpyrosmalite, feropyrosmatite, friedelite, mcgillite, schallerite, nelenite, minnesotaite, ganophyllite, eggletonite, zussmanite, parsettensite, stilpnomelane, ferrostilpnomelane, ferristilpnomelane, lennilenapeite, bannisterite, gonyerite, sepiolite, loughlinite, falcondoite, palygorskite, yofortierite, chrysotile, pecoraite or halloysite (nonplanar).

In many embodiments the carbon particles are attached to the silicate particles. In a specific example, the silicate/carbon particles of the invention include silicate particles from which carbon nanotubes extend. Such silicate/carbon particles are referred to herein as "silicate-supported carbon nanotubes" (SSCNTs) and, as discussed below, can be formed by growing carbon nanotubes on silicate particles that have a suitable catalyst associated with them.

For example, multiwall carbon nanotubes may be grown on silicate particles containing a suitable metal catalyst (e.g., $Fe^{3+}$ or $Ni^{2+}$). Examples include catalyst-rich natural phyllosilicates (e.g., iron-rich montmorillonite, etc.) and catalyst-loaded natural or synthetic phyllosilicates. For instance, montmorillonite or another phyllosilicate may be loaded with catalyst by exposing the particles one or more times to an aqueous solution of a suitable metal catalyst (e.g., $Fe^{3+}$ or $Ni^{2+}$, for instance, in the form of a suitable salt such as metallocene, nitrate or chloride salts, such as ferrocene, ferric nitrate, or nickel chloride, among others) in order to exchange the catalyst ions for cations naturally found in the phyllosilicate (e.g., sodium ions, etc.). Catalyst-containing phyllosilicate particles may be placed in a heated reactor and exposed to a carbon containing gas, such as acetylene ($C_2H_2$) to form carbon nanotubes. Processes of this type have been reported to lead to, for example, the deposition of multiwall carbon nanotubes on montmorillonite. For further information, see, e.g., K-t. Lau et al., "Cobalt hydroxide colloidal particles precipitation on nanoclay layers for the formation of novel nanocomposites of carbon nanotubes/nanoclay," *Composites Science and Technology* 66 (2006) 450-458 and A. Bakandritsos et al., "Iron changes in natural and Fe(III) loaded montmorillonite during carbon nanotube growth," *Nanotechnology* 17 (2006) 1112-1117. The former authors later reported that the resulting nanotubes are protected from aggregation by the interlayer space of nanoclay, while the montmorillonite exhibited exfoliation into silicate sheets arising from the growth of nanotubes within its interlayer spaces. See M. Lu et al., "Enhancement of Vickers hardness of nanoclay-supported nanotube reinforced novel polymer composites," *Carbon* 44 (2006) 381-392. Such SSCNTs are illustrated schematically in FIG. 1, which shows carbon nanotubes 120 extending from catalyst centers 130 on the surface of silicate particles in the form of silicate sheets 110, which arise from the montmorillonite clay particles. See K-t. Lau et al., *Composites Science and Technology* 66 (2006) 450-458. In the present invention SSCNTs may be used as-is, without the traditional removal of the nanoclay (silicate particle) support.

In accordance with the present invention, silicate/carbon particles are used to enhance various properties of implantable and insertable medical devices. Potential advantages may include one or more of the following, among others: (a) reduced permeability to molecular diffusion due to the presence of the silicate particles, particularly where planar silicate particles are employed, (b) increased cell growth due to the presence of the silicate particles (see, e.g., Aprajita Mattoo et al., "Cell Growth on Polymer-Clay Surfaces," Materials Research Society Fall 2005 meeting Boston Mass. USA, Session K5: Poster Session II: Engineered Biointerfaces, poster K5.18, who report stimulation of endothelial cells at nanoclay loadings of 10%), (c) increased tensile strength due to the presence of the carbon particles, particularly carbon nanofibers and nanotubes, (d) where SSCNTs are employed, enhanced tensile strength due to the complex shape of the particles, which may promote interlocking within a given matrix material, (e) increased hardness, and thus scratch resistance and durability (see, e.g., M. Lu et al, *Carbon* 44 (2006) 383-386 who report that SSCNTs enhance the hardness of SSCNT-polymer composites), (f) from a processing standpoint, wherein SSCNTs are employed, the silicate particle portions of the SSCNTs may inhibit aggregation of the carbon nanotube portions, while the carbon nanotube portions may likewise inhibit aggregation of the silicate particle portions; (g) in embodiments where an optional drug is supplied, the silicate particles may act as reservoirs for the drug; and (h) in embodiments where an optional drug is supplied, the nanotubes may be used to stimulate drug delivery, as nanotubes are capable of being heated. For example, carbon nanotubes may be heated by inductive heating. D. Lupu et al., *Carbon* 42 (2004) 503-507 and T. Gennett et al., *Mat. Res. Soc. Symp. Proc*, Vol. 633 (2001) A2.3.1-A2.3.6

In some embodiments of the invention, carbon particles may be derivatized with simple organic and inorganic functional groups. For example, the functionalization of carbon nanotubes with carboxyl, amino, halogen (e.g., fluoro), hydroxyl, isocyanate, acyl chloride, amido, ester, and $O_3$ functional groups has been reported, among others. See, e.g., K.

Balasubramanian and M. Burghard, "Chemically Functionalized Carbon Nanotubes," *Small* 2005, 1, No. 2, 180-192; T. Ramanathan et al., "Amino-Functionalized Carbon Nanotubes for Binding to Polymers and Biological Systems," *Chem. Mater.* 2005, 17, 1290-1295; C. Zhao et al., "Functionalized carbon nanotubes containing isocyanate groups," *Journal of Solid State Chemistry*, 177 (2004) 4394-4398; and S. Banerjee et al., "Covalent Surface Chemistry of Single-Walled Carbon Nanotubes," *Adv. Mater.* 2007, 17, No. 1, January 6, 17-29. Such groups may be provided, for example, to improve the suspendability of the carbon nanotubes in various liquids, to improve interactions with surrounding matrix materials, to improve interactions with any optional therapeutic agent, and so forth.

In some embodiments of the invention, the carbon particles are derivatized with polymers. For example, polymer derivatized carbon nanotubes have been formed using so-called "grafting to" and "grafting from" approaches.

"Grafting from" techniques typically involve (a) the attachment of polymerization initiators to the carbon particle surfaces, followed by (b) polymerization of monomers from the resulting particle-based macroinitiator. Synthesis techniques include cationic polymerization and anionic polymerization as well as radical polymerization techniques such as atom transfer radical polymerization (ATRP), stable free-radical polymerization (SFRP), nitroxide-mediated processes (NMP), and degenerative transfer (e.g., reversible addition-fragmentation chain transfer (RAFT)) processes, among others.

Suitable linking chemistries for "grafting to" techniques may be selected from following, among others: (a) linking chemistries in which polymers containing amino groups (e.g., amino terminated polymers, among others) are linked to carboxyl-, acyl-chloride-, isocyanate- or fluorine-derivatized carbon particles; (b) linking chemistries in which polymers containing hydroxyl groups (e.g., hydroxyl terminated polymers, among others) are linked to carboxyl-, acyl chloride-, isocyanate-, or fluorine-derivatized carbon particles, among others; (c) linking chemistries in which polymers containing carboxyl groups (e.g., carboxyl terminated polymers, among others) are linked to amino- and isocyanate-derivatized carbon particles, and (d) linking chemistries in which polymers containing Grignard or alkyllithium groups (e.g., Grignard or alkyllithium terminated polymers, among others) are linked to halogen-derivatized carbon particles.

For further information regarding derivitization of carbon particles, particularly nanotubes, with polymers, see, e.g., C. Wang et al., "Polymers containing fullerene or carbon nanotube structures, *Prog. Polym. Sci.* 29 (2004) 1079-1141, U.S. patent application Ser. No. 11/368,738, and the references cited therein.

Using the above and other techniques, carbon particles, including carbon nanotubes, may be derivatized with a wide range of homopolymers and copolymers. Examples of homopolymers and copolymers which may be attached to (e.g., "grafted to" or "grafted from") carbon particles for use in the present invention, include suitable polymers set forth below for use as supplemental materials, including polyalkylene oxides such as polyethylene oxide, among many others.

In some embodiments, homopolymers and copolymers attached to the carbon particles are selected to match, as closely as is practical, the properties of an associated matrix material.

As a specific example, poly(vinyl aromatic-co-alkene) polymers are described herein as examples of matrix materials, in which case it may be desirable to derivatize the particles with polyalkenes, poly(vinyl aromatics), or polyalkenes-block-poly(vinyl aromatics). Numerous examples of these polymers are described elsewhere herein. Specific examples of polyalkenes include polyalkene homopolymers and copolymers such as those containing one or more of the following: ethylene, butylene and isobutylene, among others. Specific examples of poly(vinyl aromatics) include poly(vinyl aromatic) homopolymers and copolymers such as those containing one or more of the following: styrene and alpha-methyl-styrene, among others.

As another specific example, polyether-block-polyamides are described as examples of matrix materials, in which case it may be desirable to derivatize the particles with polyethers, polyamides, or polyether-block-polyamides. Numerous examples of these polymers are described elsewhere herein. Specific examples of polyethers include polyether homopolymers and copolymers such as those containing one or more of the following: ethylene oxide, trimethylene oxide, propylene oxide and tetramethylene oxide, among others. Specific examples of polyamides include polyamide homopolymers and copolymers such as nylon 6, nylon 4/6, nylon 616, nylon 6/10, nylon 6/12, nylon 11 and nylon 12, among others.

As another specific example, ceramic materials such those comprising alumina, zirconia, glass-ceramics, calcium phosphate, or a combination thereof, among others, may be used herein as matrix materials, in which it may be desirable to derivatize the carbon particles with hydrophilic polymers, for example, polyethers such as those set forth in the prior paragraph, among others.

As another specific example, the carbon particles may be derivatized with polyelectrolyte species such as cationic, anionic and zwitterionic polyelectrolytes, or amphiphilic polymers comprising polyelectrolyte species, such that they have a positive, negative or mixed charge. See, e.g., Kong et al., *Polymer,* 46 (2005) 2472-2485 and V. A. Sinani et al., *J. Am. Chem. Soc,* 127 (2005) 3463-3472. In addition to rendering the carbon particles more hydrophilic, such derivatization steps would also produce carbon particles that can electrostatically interact with other species (e.g., charged therapeutic agents and charged matrix materials). Moreover, such particles can participate in layer-by-layer deposition processes, as discussed further below, which discussion describes many polyelectrolytes which may be suitable for derivatizing carbon particles.

In other examples, carbon nanotubes are functionalized (e.g., covalently or non-covalently conjugated) with biologically active molecules. Examples include protein-carbon nanotube conjugates, enzyme-carbon nanotube conjugates, and DNA-carbon nanotube conjugates. N. W. S. Kam et al., *Angew. Chem. Int. Ed,* 44 (2005) 1-6, L. Dai et al., *Nanotechnology,* 14 (2003) 1081-1097, and A. Merkoci et al., *Trends in Analytical Chemistry, Vol.* 24, No. 9, 2005, 826-838. In still further examples, carbon are functionalized with polyelectrolytes or other hydrophilic polymers that are conjugated with drugs, examples of which include N-(2-hydroxypropyl) methacrylamide (HPMA) copolymer-doxorubicin, HPMA copolymer-paclitaxel, HPMA copolymer-camptothecin, polyethyelene glycol (PEG)-camptothecin, polyglutamic acid-paclitaxel, HPMA copolymer-platinate and a HPMA copolymer-doxorubicin conjugate bearing additionally galactosamine. See R. Duncan et al., *Journal of Controlled Release* 1A (2001) 135-146.

In many embodiments, the silicate particles and carbon particles are held in place using one or more supplemental materials (e.g., matrix materials, etc.). Suitable supplemental materials may be selected from a variety of materials, including organic materials, inorganic materials and hybrids thereof.

The amount of supplemental material can vary widely and, where present, may represent, for example, from 0.1 wt % to 0.2 wt % to 0.5 wt % to 1 wt % to 2 wt % to 5 wt % to 10 wt % to 25 wt % to 50 wt % to 75 wt % to 90 wt % to 95 wt % to 98 wt % to 99 wt % of the particle-containing region.

Specific examples of suitable organic supplemental materials include polymeric materials (biostable or otherwise) as well as other organic materials. As used herein a "polymeric" material is one that contains polymers, typically 50 wt % or more polymers, for example, from 50 wt % to 75 wt % to 90 wt % to 95 wt % to 97.5 wt % to 99 wt % or more.

As used herein, "polymers" are molecules containing multiple copies (e.g., on the order of 5 to 10 to 50 to 100 to 1000 to 10,000 or more copies) of one or more constitutional units, commonly referred to as monomers.

Polymers may take on a number of configurations, which may be selected, for example, from cyclic, linear and branched configurations. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in composition, for instance, because a constitutional unit (i.e., monomer) is found in one polymer block that is not found in another polymer block. As used herein, a "polymer block" is a grouping of constitutional units (e.g., 5 to 10 to 25 to 50 to 100 to 250 to 500 to 1000 or more units). Blocks can be branched or unbranched. Blocks can contain a single type of constitutional unit (also referred to herein as "homopolymeric blocks") or multiple types of constitutional units (also referred to herein as "copolymeric blocks") which may be provided, for example, in a random, statistical, gradient, or periodic (e.g., alternating) distribution.

As used herein, a "chain" is a linear (unbranched) grouping of constitutional units.

Organic materials may be selected, for example, from suitable members of the following, among many others: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (crosslinked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropenes) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; various waxes; as well as blends and further copolymers of the above.

In certain embodiments, supplemental polymeric materials for use in the present invention are selected, at least in part, based on their associated Tg's (glass transition temperatures). Tg's can generally be measured by differential scanning calorimetry (DSC) (although a few exceptions exist, such as where the Tg of the polymer is above the melting or decomposition temperature of the polymer, etc.). An elevated or "high Tg polymer" is a polymer that displays a glass transition temperature that is above body temperature, more typically from 50° C. to 75° C. to 100° C. to 125° C. or more. A "low Tg polymer" is a polymer that displays a glass transition temperature that is below body temperature, more typically below about 25° C. to 0° C. to −25° C. to −50° C. or less. As used herein, body temperature is 37° C. Typically, polymers displaying low Tg's will be soft and elastic at body temperature, whereas polymers displaying high Tg's will be rigid at body temperature.

In certain embodiments, the matrix materials may include one or more block copolymers, which in turn may contain (a) one or more low $T_g$ polymer blocks (designated "L" below) and (b) one or more high $T_g$ polymer blocks (designated "H" below), the Tg of which, again, can be generally be measured by DSC. Block copolymer configurations vary widely and include, for example, the following configurations (in which H and L chains are used for illustrative purposes, although other chains having different characteristics can clearly be substituted): (a) block copolymers containing alternating chains of the type $(HL)_m$, $L(HL)_m$ and $H(LH)_m$ where m is a positive whole number of 1 or more, (b) star block copolymers containing multi-arm geometries such as $X(LH)_n$, and $X(HL)_n$, where n is a positive whole number of 2 or more, and X is a hub species (e.g., an initiator molecule residue, a residue of a molecule to which preformed polymer chains are attached, etc.), and (c) comb copolymers having a L chain backbone and multiple H side chains and those having an H chain backbone and multiple L side chains. Note that it is common to disregard the presence of non-polymeric entities, such as hub species in describing block copolymers, for example, with HL-X-LH being commonly designated as a triblock copolymer HLH.

More specific examples of block copolymers include polyether-polyamide block copolymers which include one or more low $T_g$ polyether blocks (i.e., polymer blocks containing multiple C—O—C linkages) and one or more high $T_g$ polyamide blocks (i.e., polymer chains containing multiple —NH—CO— linkages). Such block copolymers are commonly used in medical devices, for instance, in balloons, catheters and endoscopes, among others. See, for example, U.S. Pat. No. 5,556,383 to Wang et al. for more information. Many polyether-polyamide block copolymers have excellent mechanical properties, are stable, and are readily processed (e.g., by melt or solution processing). Further specific examples of polyether-polyamide block copolymers include those containing (a) one or more polyether blocks selected from homopolymer blocks such as polyethylene oxide, poly (trimethylene oxide), poly(propylene oxide) and polytetramethylene oxide, and copolymer blocks such as those containing two or more of the following: ethylene oxide, trimethylene oxide, propylene oxide and tetramethylene oxide, (b) one or more polyamide blocks selected from nylon homopolymer blocks and copolymer blocks such as nylon 6, nylon 4/6, nylon 6/6, nylon 6/10, nylon 6/12, nylon 11 and nylon 12. For example, polytetramethylene oxides-nylon-12 block copolymers are available from Elf Atochem as PEBAX.

Further specific examples of block copolymers further include polyalkene-poly(vinyl aromatic) block copolymers which include one or more low $T_g$ polyalkene blocks and one or more high $T_g$ poly(vinyl aromatic) blocks, including those containing (a) one or more polyalkene homopolymer or copolymer blocks, which may contain, for example, one or more of ethylene, butyl ene and isobutylene, among others and (b) one or more poly(vinyl aromatic) homopolymer or copolymer blocks, which may contain, for example, one or more of styrene and alpha-methyl-styrene, among others. For instance, polyisobutylene-polystyrene block copolymers can be employed, including polystyrene-polyisobutylene-polystyrene triblock copolymer (SIBS), which are described in U.S. Pat. No. 6,545,097 to Pinchuk et al.

Further specific examples of block copolymers further include block copolymers having one or more high Tg poly (meth)acrylate blocks and one or more low Tg poly(meth) acrylate blocks (where "(meth)acrylate" denotes acrylate or methacrylate).

Low Tg (meth)acrylate blocks can be selected from homopolymer and copolymer blocks of one or more of the following (presented along with the reported Tg of the homopolymer): (1) low Tg acrylic monomers including: (a) alkyl acrylates such as methyl acrylate (Tg 10° C.), ethyl acrylate (Tg −24° C.), propyl acrylate, isopropyl acrylate (Tg −11° C., isotactic), butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.), dodecyl acrylate (Tg −3° C.) and hexadecyl acrylate (Tg 35° C.), (b) arylalkyl acrylates such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylates such as 2,2,2-trifluoroethyl acrylate (Tg −10° C.) and (e) cyano-alkyl acrylates such as 2-cyanoethyl acrylate (Tg 4° C.) and (2) low Tg methacrylic monomers including (a) alkyl methacrylates such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylates such as diethylaminoethyl methacrylate (Tg 20° C.) and 2-tert-butyl-aminoethyl methacrylate (Tg 33° C.).

High Tg (meth)acrylate blocks can be selected from homopolymer and copolymer blocks of one or more of the following (presented along with the reported Tg of the homopolymer): (1) high Tg methacrylic monomers including (i) alkyl methacrylates such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (ii) aromatic methacrylates such as phenyl methacrylate (Tgl 110° C.) and including aromatic alkyl methacrylates such as benzyl methacrylate (Tg 54° C.), (iii) hydroxyalkyl methacrylates such as 2-hydroxyethyl methacrylate (Tg 57° C.) and 2-hydroxypropyl methacrylate (Tg 76° C.), (iv) additional methacrylates including isobornyl methacrylate (Tg 110° C.) and trimethylsilyl methacrylate (Tg 68° C.) and (2) high Tg acrylic monomers including (a) certain acrylic acid esters such as tert-butyl acrylate (Tg 43-107° C.), hexyl acrylate (Tg 57° C.) and isobornyl acrylate (Tg 94° C.); and (b) other acrylic-acid derivatives including acrylonitrile (Tg 125° C.).

One example of a preferred (meth)acrylate polymer is poly (methyl methacrylate-b-butyl acrylate-b-methyl methacrylate).

In certain embodiments of the invention, the particle-containing regions of the invention further comprise a therapeutic agent.

Depending on the nature of the therapeutic agent, the nature of the silicate particles, the nature of the carbon particles, and the nature of any supplemental materials (e.g., polymeric and/or a ceramic matrix materials, etc.), the therapeutic agent may be maintained in association with the layered silicate particles by any of a number of mechanisms including, for example, non-covalent interactions such as Van der Waals interactions, hydrophilic/hydrophobic interactions, electrostatic interactions (e.g., ion-ion, ion-dipole and dipole-dipole interactions, including hydrogen bonding), and so forth.

In some embodiments of the invention, for example, where the therapeutic agent and one or more other constituents of the particle-containing layer (e.g., silicate particles, carbon particles and/or supplemental materials) are both relatively hydrophilic (or are both relatively hydrophobic), the therapeutic agent will readily associate with the one or more other constituents. For instance, anions associated with the silicate particles may exhibit a strong attraction for polar and/or cationic molecules, and thus for therapeutic agents having polar and/or cationic characteristics. As another example, carbon particles, including carbon nanotubes, can be derivatized with various species (e.g., charged groups, charged polymers such as cationic, anionic or zwitterionic polyelectrolytes, polar polymers, nonpolar polymers, etc.) to increase the affinity of the carbon particles for the therapeutic agent. Similarly, where one or more polymeric matrix materials are provided, the matrix materials may be selected not only based on compatibility with the silicate particles and/or the carbon particles, but also based on compatibility with the therapeutic agent.

In some embodiments, for example, where the therapeutic agent is relatively hydrophobic, the silicate particles may be rendered more hydrophobic by exchanging inorganic cations associated with the silicate particles with one or more species having both a positive charge and a hydrophobic domain. Examples of such species that have been used for this purpose include alkylammonium ions, for instance, tertiary and quaternary alkylammonium ions, such as trimethyl ammonium ions and hexadecyltrimethylammonium (HDTMA) ions. By replacing the inorganic cations associated with the silicate particles with these species, the silicate particles are rendered more hydrophobic, thereby enhancing the association between the relatively hydrophobic therapeutic agent and the silicate particles.

Typically, particle-containing regions in accordance with the present invention are formed from a suspension that contains the silicate particles and carbon particles described herein (which, as noted above, are referred to herein collectively as "silicate/carbon particles," whether attached or unattached to one another).

Examples of particle suspensions include suspensions in polymer melts (e.g., where polymers having thermoplastic characteristics are employed as matrix materials), suspensions in polymer solutions (e.g., where polymers are employed as matrix materials that are dissolvable in an aqueous, organic or aqueous/organic solvent), suspensions in curable polymer systems (e.g., where polymers are employed as matrix materials that are based on systems such as epoxy systems which undergo chemical cure, and systems that cure upon exposure to radiation, including UV light and heat), suspensions that include precursors to ceramic matrix materials, as well as suspensions that do not contain matrix materials, among others.

In embodiments where the particles of the invention are elongated (e.g., where the silicate/carbon particles comprise carbon nanotubes, carbon nanofibers and/or elongated silicate particles), they may be aligned, typically while in a suspension. For example, the elongated particles may be aligned by shear forces present during formation of the particle-containing regions of the invention, they may be aligned by the application of an electric field during formation of the particle-containing regions of the invention, and so forth. Once the particles are aligned, the liquid suspension may be solidified, if necessary, to fix the elongated particles in their new orientation.

As one example, elongated particles may be incorporated into balloons or balloon coatings to increase strength. In these situations, it may be desirable to align the elongated particles primarily in the direction of the stress vector (e.g., in a circumferential orientation) to further enhance strength. As another example, it may be desirable to provide multiple layers containing elongated particles, for example, a first layer having the elongated particles aligned in a direction that is perpendicular to the elongated particles in an overlying second layer. As another example, elongated particles, particularly carbon nanotubes, may enhance the electrical and/or thermal conductivity of the particle-containing region. Anisotropy of either of these characteristics may be very useful within medical devices. For instance, catheters are known through which one flushes a coolant with the objective of cooling the surrounding tissue in order to minimize tissue damage after a heart attack. In such catheters, it would be desirable to increase the thermal conductivity from the catheter to the surrounding tissue as much as possible at the distal section of the catheter. Carbon nanotubes are known to increase the thermal conductivity of a polymer matrix. When such nanoparticles are aligned in a radial outward direction (e.g., with respect to the catheter shaft), one may achieve enhanced conductivity relative to other nonrandom and random spatial distributions.

As noted above, in some embodiments, the elongated particles are aligned by the application of an electric field during formation of the particle-containing regions of the invention. By way of background, if an uncharged, polarizable particle (which may be, for example, an uncharged, polarizable dielectric, semi-conductive or conductive particle) is placed in an electric field, there will be an induced positive charge on one side of the particle and an induced negative charge, of the same magnitude as the induced positive charge, on the other side of the particle. The positive charge will experience a first force; the negative charge will experience a second force in the opposite direction of the first force. For elongated particles, this causes a torque on the particle that tends to align it relative to the electric field. For example, both carbon nanotubes and carbon nanofibers have been used as conductive fillers in epoxy systems (in particular, epoxy systems based on bisphenol-A resin and amine hardener), and AC electric fields have been used to induce the formation of aligned carbon nanotube/nanofiber networks in such systems. DC electric fields were also shown to induce the formation of aligned carbon nanotube networks, although these were less uniform and less aligned than those achieved with the use of AC fields. The quality of the nanotube networks and the resulting bulk conductivity of the composite material were enhanced with increasing field strength. Moreover, electrical anisotropy was observed in the nanofiber-containing composites, and electrical anisotropy was expected to be present in the nanotube-containing composites, based on the observed orientation of the field-induced nanotube networks. For further information, see T. Prasse, "Electric anisotropy of carbon nanofibre/epoxy resin composites due to electric field induced alignment," *Composites Science and Technology* 63 (2003) 1835-1841; and C. A. Martin et al, "Electric field-induced aligned multi-wall carbon nanotube networks in epoxy composites," *Polymer* 46 (2005) 877-886.

In accordance with the invention, applying liquid suspensions containing elongated carbon particles to a substrate in multiple layers allows one to change the direction of the particles from layer to layer. For example, one may change the direction of the electric field between layers such that the particles within alternating layers are aligned orthogonally to each other. One can, of course, employ a single preferential direction for a single layer or for multiple layers.

Where the elongated carbon particles have a net charge, it may be desirable to employ an AC electric field to minimize or eliminate migration of the particles within the suspension (e.g., to prevent electrode agglomeration of the particles). On the other hand, it may be desirable to promote gradients in elongated particle density, as well as particle alignment, in which case DC electric fields, or combinations of DC and AC electric fields (e.g., by applying an alternating voltage, which a DC bias), may be employed.

Various electrode arrangements are described in U.S. Ser. No. 11/368,738 to Weber et al. by which elongated particles can be (a) aligned in a planar particle-containing region, including an arrangement using orthogonal electrodes such that the direction of alignment can be varied from layer to layer and (b) aligned in a tubular/annular particle-containing region (e.g., along the axis of the tubular/annular region, around the circumference of the tubular/annular region, radially with respect to the tubular/annular region, etc.).

Whether or not particles have been successfully aligned during formation of the particle-containing regions of the invention can be determined, for example, by microscopic analysis of cross-sections of the particle-containing regions (e.g., using transmission electron microscopy). In some instances, particle alignment can be inferred from significant anisotropy in electrical, mechanical or other physical measurements, for example, exhibiting directional differences of at least 20% to 50% to 100% or more.

Various specific techniques for forming medical devices in accordance with the invention will now be discussed.

In some embodiments, polymer processing techniques are employed. Examples of polymer processing techniques include those techniques in which a silicate/carbon particle suspension based on a solution (e.g., where solvent-based processing is employed), melt (e.g., where thermoplastic processing is employed), or other liquid-polymer-based composition (e.g., where a curable composition is employed) is applied to a substrate. For example, the substrate can correspond to all or a portion of a medical article surface to which a layer is applied. The substrate can also be, for example, a template, such as a mold, from which the particle-containing region is separated after formation. In other embodiments, for example, extrusion and co-extrusion techniques, particle-containing regions may be formed from such suspensions without the aid of a substrate. Some specific examples of polymer processing techniques include molding, casting and coating techniques such as injection molding, blow molding, solvent casting, dip coating, spin coating, spray coating, coating with an applicator (e.g., by roller or brush), web coating, screen printing, and ink jet printing, as well as extrusion and co-extrusion into sheets, fibers, rods, tubes and other cross-sectional profiles of various lengths.

In some of these embodiments, an electric field is applied to align the elongated particles in suspension prior to immobilization of the same, for example, due to solidification of the polymer component of the suspension (e.g., as a result of cooling, solvent evaporation, curing/cross-linking, etc.)

Particle-containing regions in accordance with the present invention may also be created by processes commonly known as layer-by-layer techniques, by which a variety of substrates may be coated using charged materials via electrostatic self-assembly. In the layer-by-layer technique, a first layer having a first surface charge is typically deposited on an underlying substrate (e.g., a medical device or portion thereof, a template, such as a mold, from which the particle-containing regions is separated after formation, etc.), followed by a second layer having a second surface charge that is opposite in sign to the surface charge of the first layer, and so forth. The charge on the outer layer is reversed upon deposition of each sequential layer. Commonly, 5 to 10 to 25 to 50 to 100 to 200 or more layers are applied in this technique, depending on the desired thickness.

Layer-by-layer techniques generally employ charged polymer species, also referred to as polyelectrolytes. Specific examples of polyelectrolyte cations (also known as polycations) include protamine sulfate polycations, poly(allylamine) polycations (e.g., poly(allylamine hydrochloride) (PAH)), polydiallyldimethylammonium polycations, polyethyleneimine polycations, chitosan polycations, gelatin polycations, spermidine polycations and albumin polycations, among many others. Specific examples of polyelectrolyte anions (also known as polyanions) include poly(styrenesulfonate) polyanions (e.g., poly(sodium styrene sulfonate) (PSS)), polyacrylic acid polyanions, sodium alginate polyanions, eudragit polyanions, gelatin polyanions, hyaluronic acid polyanions, carrageenan polyanions, chondroitin sulfate polyanions, and carboxymethylcellulose polyanions, among many others.

Further information regarding layer-by-layer techniques are described, for example, in 20070154513 to Atanasoska et al. and 20050208100 to Weber et al.

In the present invention, the layer-by-layer technique will also employ silicate/carbon particles having an overall negative or positive charge. As a specific example, a suspension of negatively charged SSCNTs (with or without an accompanying anionic polyelectrolyte in the suspension) may be employed for the deposition of one or more negatively charged layers. Alternatively (or in addition) a suspension of positively charged SSCNTs (with or without an accompanying cationic polyelectrolyte) may be employed for the deposition of one or more positively charged layers. For example, SSCNTs may be formed as described above, followed by functionalization of the carbon nanotubes with anionic or cationic species (which may be polymeric or non-polymeric, preferably anionic or cationic polyelectrolyte species) as is known in the carbon nanotube art. In these embodiments, a polymeric "matrix" comprising polyelectrolytes holds the SSCNTs in place. In certain embodiments, the carbon nanotubes may be aligned during the deposition process by applying an electric field.

As previously discussed, in addition to organic materials such as polymers, examples of supplemental materials for use in the present invention also include inorganic materials, including ceramic materials. Ceramic processing may proceed by a variety of techniques, such as those in which liquid suspensions of ceramic particles and silicate/carbon particles are processed (e.g., colloid based processing). Suitable examples of ceramic processing techniques based on liquid suspensions may be selected, for example, from the coating techniques such as dip-coating, spray coating, coating with an applicator (e.g., by roller or brush), spin-coating, ink-jet printing or screen printing, as well as various casting/molding techniques, including slip casting, tape casting, direct coagulation casting, electrophoretic casting, gel casting, hydrolysis assisted solidification, aqueous injection molding, and temperature induced forming. Analogous to the above techniques, the liquid suspension is subsequently solidified. In some embodiments, elongated particles within the suspension may be aligned using an electric field prior to solidification of the suspensions. In this way, these techniques may be used to form particle-containing regions in accordance with the invention, typically in coordination with a substrate, such as a medical device or a portion thereof or a template such as a mold from which the particle-containing regions is separated after formation.

Sol-gel processing will now be described in more detail, with the understanding that other ceramic processing techniques, including other techniques based on liquid suspensions of solid ceramic particles, may be employed. Further information concerning sol-gel materials can be found, for example, in Viitala R. et al., "Surface properties of in vitro bioactive and non-bioactive sol-gel derived materials," *Biomaterials*, 2002 August; 23(15):3073-86.

In a typical sol-gel process, precursor materials, typically selected from inorganic metallic and semi-metallic salts, metallic and semi-metallic complexes/chelates, metallic and semi-metallic hydroxides, and organometallic and organo-semi-metallic compounds such as metal alkoxides and alkoxysilanes, are subjected to hydrolysis and condensation reactions (also referred to sometimes as polymerization reactions), thereby forming a "sol" (i.e., a suspension of solid particles within a liquid).

For example, an alkoxide of choice (such as a methoxide, ethoxide, isopropoxide, te/T-butoxide, etc.) of a semi-metal or metal of choice (such as silicon, aluminum, zirconium, titanium, tin, hafnium, tantalum, molybdenum, tungsten, rhenium, iridium, etc.) may be dissolved in a suitable solvent, for example, in one or more alcohols. Subsequently, water or another aqueous solution, such as an acidic or basic aqueous solution (which aqueous solution can further contain organic solvent species such as alcohols) is added, causing hydrolysis and condensation to occur. If desired, additional agents can be added, such as agents to control the viscosity and/or surface tension of the sol. Moreover, silicate/carbon particles are also provided within the sol, in accordance with the invention.

Further processing of the sol enables solid materials to be made in a variety of different forms. For instance, coatings can be produced on a substrate by spray coating, coating with an applicator (e.g., by roller or brush), spin-coating, dip-coating, ink-jet printing, screen printing, and so forth, of the sol onto a substrate, whereby a "wet gel" is formed. Monolithic wet gels can be formed, for example, by placing the sol into or onto a mold or another form (e.g., a sheet). Particles within the wet gel may be aligned as discussed elsewhere herein during the wet gel stage. The wet gel is then dried. The structure may then optionally heated, for example, to a temperature ranging anywhere from about 150° C. to about 600° C. or higher, to form a heat-treated particle-containing region. At the lower end of this range, the ceramic components are consolidated and strengthened as a result of the heat treatment process, but the temperatures are sufficiently low that many therapeutic agents (where present) will remain intact. Higher temperatures result in greater consolidation.

In one aspect of the invention, sol-gel processing is combined with layer-by-layer processing. For further information on layer-by-layer/sol-gel processing, see, e.g., *Colloids and Colloid Assemblies*, Wiley-VCH, edited by Frank Caruso, ISBN 3-527-30660-9, pp. 266-269, D. Wang and F. Caruso, *Chem. Mater.* 2002, 14, 1909-1913, D. Wang et al., "Synthesis of Macroporous Titania and Inorganic Composite Materials from Coated Colloidal Spheres A Novel Route to Tune Pore Morphology," *Chem. Mater.* 2001, 13, 364-371; and WO 02/074431 to Caruso.

For example, a multilayer particle-containing region may first be formed as described above, which region contains (a) charged silicate/carbon particles in accordance with the invention (e.g., those comprising nanotubes with conjugated charged species such as polylelectrolytes, etc.) and (b) one or more polyelectrolytes. As a specific example, the multilayer region may contain among other possibilities: (a) a combination of a positively charged polyelectrolyte such as poly(allylamine hydrochloride) (PAH) and negatively charged SSCNTs, (b) a combination of a negatively polyelectrolyte such as poly(sodium 4-styrenesulfonate) (PSS) and positively charged SSCNTs, or (c) both positively and negatively charged polyelectrolytes (e.g., PAH and PSS) in combination with SSCNTs that are positively charged, negatively charged or both.

In a next step, a sol-gel-type process is carried out within the polyelectrolyte layers. For example, a structure comprising/consisting of a multilayer particle-containing region like that described in the prior paragraph may be immersed in a sol-gel precursor solution of a semi-metal or metal alkoxide in anhydrous alcohol solvent or in a water-alcohol solvent having a high alcohol content (i.e., a solvent in which the water concentration is too low for hydrolysis-condensation reactions to occur), which may also include an acidic or basic species. In one specific example, such a structure is immersed in the sol-gel precursor solution for several hours (e.g., 10 to 20 hours). One example of a suitable sol-gel precursor solution for this purpose is one wherein 2 g tetraethoxysilane (TEOS) is combined with 100 mL ethanol (anhydrous, denatured) and mixed, followed by the addition of 10 mL DI water and 1 mL ammonium hydroxide (25% in water), followed by further mixing.

Without wishing to be bound by theory of operation, the high charge density of the polyelectrolyte groups are believed to cause the multilayer particle-containing region to have a water concentration that is higher than that of the surrounding sol-gel precursor solution (e.g., by attracting water molecules out of the sol-gel precursor solution and/or by retaining water molecules during prior processing). Upon diffusion into the multilayer particle-containing region, the sol-gel precursor encounters an environment of increased water concentration in which the hydrolysis and condensation can take place. The multilayer particle-containing region then swells, due to the in-situ reaction of the sol-gel precursor within the layers. However, the charge density also decreases due to the swelling, causing a reduction in water concentration, which eventually stops the sol-gel reaction. Regardless of the exact mechanism, the resulting multilayer particle-containing region, which is a polyelectrolyte/ceramic/SSCNT hybrid region, is relatively uniformly thick, and its thickness is dependent upon the number of layers within the polyelectrolyte coating (with more layers leading to thicker coatings).

After exposure to the sol-gel solution, the structure may then optionally heated, for example, to a temperature ranging anywhere from about 150° C. to about 600° C. or higher, to form a heat-treated particle-containing region. At the higher end of the range, the particle-containing region has a high proportion of ceramic species and SSCNTs (e.g., containing 90 wt % or more of these species, for example, from 95 wt % to 98 wt % to 99 wt % to 99.5 wt % to 99.9 wt % or more), with substantially all of the polyelectrolyte component of the coating being out-gassed from the structure in a process sometimes referred to as calcination. At the lower end, the ceramic components are consolidated and strengthened as a result of the heat treatment process, but the temperatures are sufficiently low that many polyelectrolytes (and many therapeutic agents, where present) will remain intact.

In still other embodiments, particle-containing regions in which polyelectrolytes and silicate/carbon particles are not arranged in a layer-by-layer fashion are treated as described above. For example, a solution comprising polyelectrolyte and particles in accordance with the invention, as well as an optional therapeutic agent, may be coated onto a substrate, cast into a desired shape, extruded into fibers, rods, tubes, and so forth. After drying, the resulting structure is then treated as described above (e.g., immersed in sol gel precursor solution and optionally heat treated). In a specific example, extruded regions that contain one or more polyelectrolyte species, silicate/carbon particles in accordance with the invention, and one or more optional therapeutic agents are formed using techniques such as those described in Pub. No. US 2007/0067882, followed by treatment as described above.

As indicated above, in certain embodiments of the invention, one or more therapeutic agents may be incorporated over, within or beneath the particle-containing regions. In some embodiments, the therapeutic agent is provided within the particle-containing regions in which case the therapeutic agent may be incorporated into the particle-containing regions during their formation (e.g., by adding at least one therapeutic agent to a silicate/carbon-particle-containing suspension prior to solidification) or after their formation (e.g., by exposing the as-formed particle-containing region to a solution containing one or more therapeutic agents such that the therapeutic agent is taken up by the particle-containing region, etc.)

"Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Exemplary therapeutic agents for use in connection with the present invention include: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anticoagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, fiavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, All, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ft) phospholipids including phosphorylcholine, phosphatidylinositol and phosphatidylcholine, (gg) VLA-4 antagonists and VCAM-1 antagonists.

Numerous therapeutic agents, not necessarily exclusive of those listed above, have been identified as candidates for vascular treatment regimens, for example, as agents targeting restenosis (antirestenotic agents). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including a-antagonists such as prazosin and bunazosine, P-antagonists such as propranolol and a/p-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k)

coagulation pathway modulators including heparinoids such as heparin, low molecular weight heparin, dextran sulfate and P-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfmpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (O) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfm, rostaporfm, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-P pathway agents such as polyanionic agents (heparin, fucoidin), decorin, and TGF-p antibodies, EGF pathway agents such as EGF antibodies, receptor antagonists and chimeric fusion proteins, TNF-a pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Some preferred therapeutic agents include taxanes such as paclitaxel (including particulate forms thereof, for instance, protein-bound paclitaxel particles such as albumin-bound paclitaxel.nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abcix-imab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Numerous additional therapeutic agents useful for the practice of the present invention are also disclosed in U.S. Pat. No. 5,733,925 to Kunz, the entire disclosure of which is incorporated by reference.

Example 1

100 grams of Cloisite® 3 OB (a natural montmorillonite modified with a quaternary ammonium salt; Southern Clay Products, 1212 Church Street, Gonzales, Tex., USA) is dehydrated at 250° C. for 1 h in air. The dehydrated Cloisite® and 160 g of Iron(III) acetylacetonate (Sigma Aldrich) are placed into a quartz reactor and heated up to 150° C. for 30 minutes under a Argon atmosphere. Subsequently the reactor is cooled in a stream of nitrogen to room temperature. The Iron is reduced in a quartz reactor by exposing the modified Cloisite® with the deposited iron-acetylacetonate to a flow of hydrogen and argon (1:1 volume ratio) at 450° C. for 2.5 h, causing iron nanoparticles to be created on the montmorillonite surface. The modified nanoclay is then placed in a quartz reactor and exposed to a stream of $C_2H_2$ at 700° C. for 1 h to create carbon nanostructures on the silica\iron structures. 1 gram of the thus modified Cloisite® particles are mixed in 1 liter of toluene with 1 gram therapeutic agent (paclitaxel) and 5 grams triblock copolymer (poly[styrene-6-isobutylene-6-styrene] as described in M. Gyor et al., *J. of Macromolecular Scl, Pure and Applied Chem.*, 1992, A29(8), 639 and in U.S. Pat. App. No. 2002/0107330 to Pinchuk et al.). This solution is then sprayed on an Express® stent (Boston Scientific, Natick, Mass., USA), creating a 10 micrometer thick film on the stent to serve as a modified drug eluting coating.

Example 2

Carbon-nanotube-modified Cloisite® particles are created as described Example 1. A solution is then formed by mixing 1 gram of the thus modified Cloisite® particles and 1 gram therapeutic agent (paclitaxel) with 1 liter of a 3% solution of polyether block amide (e.g., Pebax® 2533, Pebax® 3533, or a combination thereof) in ethanol, which is then sprayed onto a Pebax® or nylon balloon.

Although various embodiments of the invention are specifically illustrated and described herein, it will be appreciated that modifications and variations of the present invention are covered by the above teachings without departing from the spirit and intended scope of the invention.

What is claimed is:

1. An implantable or insertable medical device comprising:
   a particle-containing region that comprises carbon nanotubes that are attached to silicate particles;
   a therapeutic agent disposed within the particle-containing region; and
   wherein the silicate particles are a reservoir for the therapeutic agent.

2. The medical device of claim 1, wherein said medical device is selected from a balloon, a catheter and a stent.

3. The medical device of claim 1, wherein at least a portion of said particle-containing region is disposed on a substrate.

4. The medical device of claim 3, wherein said substrate is selected from a balloon, a catheter tube and a stent.

5. The medical device of claim 3, wherein said substrate is selected from a metallic substrate and a polymeric substrate.

6. The medical device of claim 1, comprising a plurality of particle-containing regions.

7. The medical device of claim 6, comprising a substrate, a first particle-containing layer disposed over the substrate and a second particle-containing layer disposed over the first particle-containing layer.

8. The medical device of claim 1, wherein the particle-containing region further comprises a supplemental material.

9. The medical device of claim 1, wherein the supplemental material is a ceramic material.

10. The medical device of claim 9, wherein the ceramic material is selected from oxides of one or more of silicon, aluminum, iridium, zirconium, and combinations thereof.

11. The medical device of claim 8, wherein the supplemental material is a polymeric material.

12. The medical device of claim 11, wherein the polymeric material comprises a block copolymer.

13. The medical device of claim 12, wherein the block copolymer is selected from (a) a block copolymer that comprises a polyalkene block and a poly(vinyl aromatic) block, (b) a block copolymer that comprises a polyether block and a polyamide block and(c) a block copolymer that comprises high Tg poly(meth)acrylate block and a low Tg poly(meth) acrylate block.

14. The medical device of claim 11, wherein said polymeric material comprises a polyelectrolyte.

15. The medical device of claim 1, wherein said particle-containing region comprises carbon nanotubes having a first charge and polyelectrolytes having a second charge that is opposite to that of said first charge.

16. The medical device of claim 1, wherein the silicate particles are in the form of silicate sheets.

17. The medical device of claim 16, wherein the silicate sheets are formed from natural or synthetic phyllosilicate particles.

18. The medical device of claim 17, wherein the phyllosilicate particles are montmorillonite particles.

19. The medical device of claim 1, wherein the particle-containing region comprises derivatized carbon nanotubes.

20. The medical device of claim 19, wherein the derivatized carbon nanotubes are polymer-derivatized carbon nanotubes.

21. The medical device of claim 19, wherein the derivatized carbon nanotubes are polyelectrolyte-derivatized carbon nanotubes.

22. The medical device of claim 1, wherein the therapeutic agent is a charged therapeutic agent.

23. The medical device of claim 1, wherein the therapeutic agent is an antirestenotic agent.

24. The medical device of claim 1, wherein the elongated carbon particles are electrically aligned.

25. The medical device of claim 24, wherein the particle-containing region is an annular particle-containing region having an axis and wherein the elongated particles are aligned parallel to the axis of the annular particle-containing region, aligned radially with respect to the axis of said annular particle-containing region, or aligned circumferentially with respect to the annular particle-containing region.

* * * * *

UNITED STATES PATENT AND TRADEMARK OFFICE
CERTIFICATE OF CORRECTION

PATENT NO.        : 8,480,729 B2
APPLICATION NO.   : 12/205647
DATED             : July 9, 2013
INVENTOR(S)       : Liliana Atanasoska et al.

Page 1 of 1

It is certified that error appears in the above-identified patent and that said Letters Patent is hereby corrected as shown below:

In the Specification

Column 5
Line 12: delete "sanbomite" and insert therefor -- sanbornite --

Signed and Sealed this
Tenth Day of December, 2013

Margaret A. Focarino
*Commissioner for Patents of the United States Patent and Trademark Office*